United States Patent [19]

Cini et al.

[11] Patent Number: 5,130,298
[45] Date of Patent: Jul. 14, 1992

[54] STABILIZED COMPOSITIONS CONTAINING EPIDERMAL GROWTH FACTOR

[75] Inventors: John K. Cini, Bethlehem Township, Northhampton County, Pa.; Amy L. Finkenaur, Somerville, N.J.

[73] Assignee: Ethicon, Inc., Somerville, N.J.

[21] Appl. No.: 353,131

[22] Filed: May 16, 1989

[51] Int. Cl.$^5$ .................... A61K 35/22; A61K 37/36
[52] U.S. Cl. .................... 514/12; 530/324; 530/399; 514/2; 514/21
[58] Field of Search .............. 530/399, 324; 514/2, 514/12, 21

[56] References Cited

U.S. PATENT DOCUMENTS

| | | | |
|---|---|---|---|
| 3,887,704 | 6/1975 | Lichtenstein | 514/2 X |
| 4,476,118 | 10/1984 | Brange et al. | 514/3 |
| 4,717,717 | 1/1988 | Finkenauer | 530/399 |
| 4,764,592 | 8/1988 | Massey et al. | 530/303 X |
| 4,816,568 | 3/1989 | Hamilton et al. | 530/399 |

OTHER PUBLICATIONS

Chem. Abstracts, vol. 108, 1988 (Effective Date of Article, 1987), 52332C, 3442-3CS, Konno et al.

*Primary Examiner*—Howard E. Schain
*Assistant Examiner*—a
*Attorney, Agent, or Firm*—Richard J. Grochala

[57] ABSTRACT

The present invention provides a pharmaceutical composition comprising a pharmaceutically effective amount of human epidermal growth factor (EGF) and an amount of a pharmaceutically acceptable metal cation, such as zinc, which is sufficient to prevent the degradation of said EGF.

11 Claims, 1 Drawing Sheet

STABILIZED COMPOSITIONS CONTAINING EPIDERMAL GROWTH FACTOR

BACKGROUND OF THE INVENTION

The present invention concerns pharmaceutical compositions containing human epidermal growth factor (EGF) and methods for making and using such compositions. In particular, the invention relates to such pharmaceutical compositions having increased stability as a result of being combined with a metal cation, such as zinc.

Human EGF (also known as urogastrone) is a 53 amino acid polypeptide growth factor that has mitogenic activity for a number of kinds of cells, including epithelial and mesenchymal cells. Variants of the human EGF polypeptide have been reported, such as the 52 amino acid gamma-urogastrone. EGF has been reported to be useful in increasing the rate of wound healing as a result of its mitogenic effect. EGF has also been reported as being useful for treating gastric ulcers. A review of EGF is provided by Carpenter et al., in "Epidermal Growth Factor, Its Receptor and Related Proteins," Experimental Cell Research, 164:1-10 (1986).

An important objective in the therapeutic use of EGF is the development of a stable pharmaceutical EGF formulation that has a long shelf life and is capable of remaining as a predominantly active single species of EGF over a long period of time. However, because of the inherent instability of EGF, difficulties have been encountered in developing such a stable EGF formulation. For instance, EGF loses biological activity in the presence of moisture. U.S. Pat. No. 4,717,717 describes compositions and methods for stabilizing EGF against such a loss of biological activity. Also, human EGF loses activity over time and produces multiple species of the EGF molecule, which have been identified by high performance liquid chromatography (HPLC). These multiple species of EGF are believed to be breakdown products resulting from the degradation of EGF or derivatives resulting from the chemical modification of EGF. It is believed that there are at least three such degradation products, some or all of which have reduced EGF biological activity. Incubation of EGF at 45° C. accelerates the formation of the degradation products normally found with long term storage at ambient temperature. Such degradation, and the associated loss of biological activity of EGF, is a disadvantage because it makes it impractical to store aqueous or solid preparations of EGF over extended periods of time.

The present invention provides a means for reducing the degradation of the EGF molecule and the resulting loss of biological activity.

SUMMARY OF THE INVENTION

The present invention provides a pharmaceutical composition comprising a pharmaceutically effective amount of human epidermal growth factor (EGF) and an amount of a pharmaceutically acceptable metal cation sufficient to prevent the degradation of said EGF. In a preferred embodiment, the metal cation is the divalent zinc ion. Also provided is a crystalline EGF composition which comprises a salt of a complex of zinc and EGF which is stabilized against degradation and loss of biological activity. The present invention further provides methods for stabilizing EGF by mixing the EGF with a suitable metal cation which is capable of preventing the degradation of the EGF.

A BRIEF DESCRIPTION OF THE FIGURE

FIG. 1 is a chromatogram which depicts the relationship of EGF Peaks C, D, X and Y after a solution of aged EGF was analyzed by reverse phase HPLC.

DETAILED DESCRIPTION OF THE INVENTION

Figure 1:
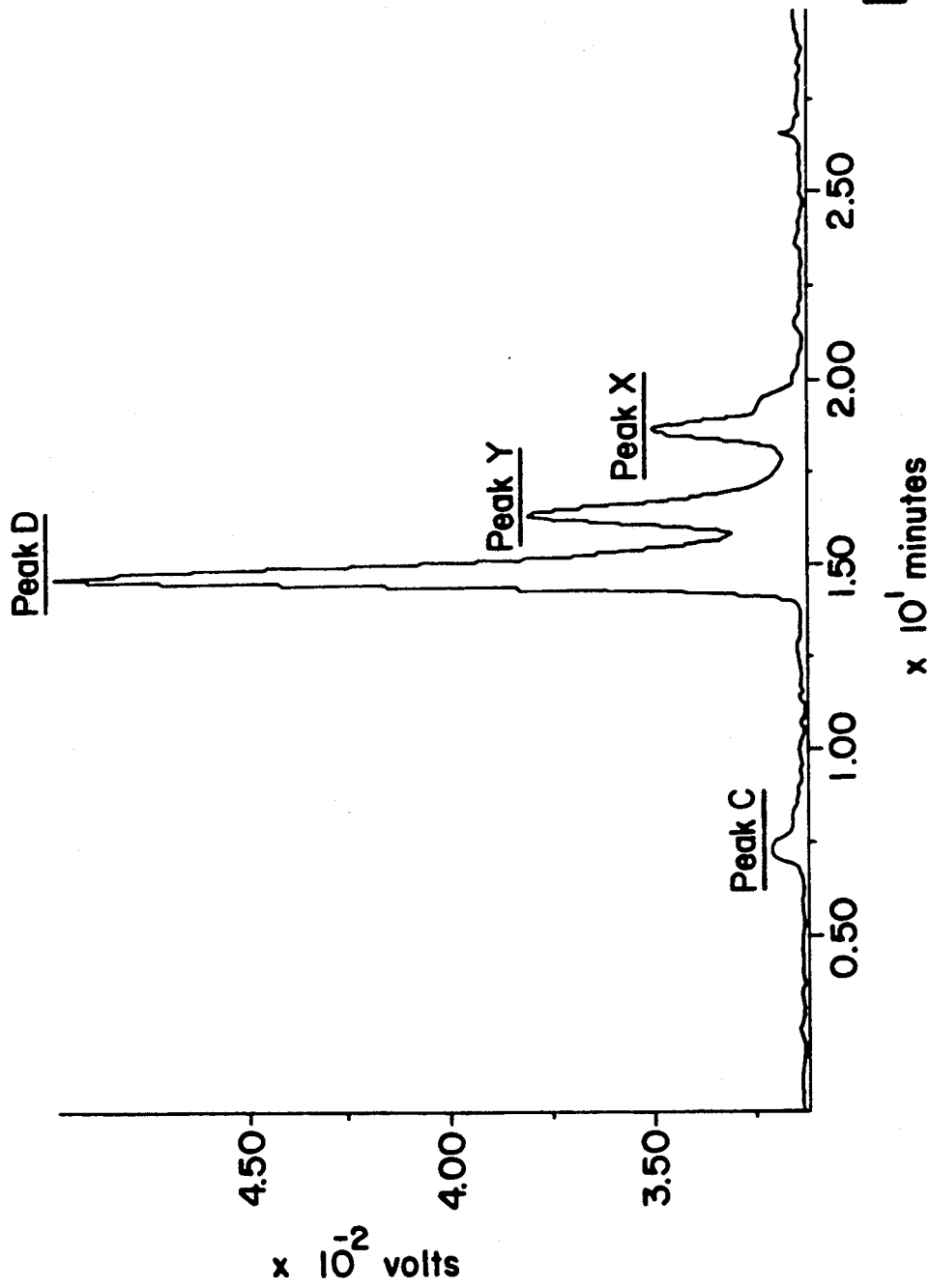

Human EGF refers to the EGF having that polypeptide sequence, or any substantial portion thereof, as set forth in Urdea, M. S. et al., Proc. Natl. Acad. Sci. U.S.A. 80:6461-6465 (1983). Human EGF also refers to any human EGF variants, such as gamma-urogastrone. EGF may be isolated from natural sources, produced using recombinant DNA techniques or prepared by chemical synthesis. It is contemplated that biologically active fragments, analogs or man-made chemically synthesized derivatives of EGF may be used in the present invention instead of the entire naturally occurring molecule, provided that such fragments, analogs or derivatives retain the biological activity of naturally occurring EGF. EGF biological activity refers to the mitogenic activities for epithelial and mesenchymal cells and the inhibition of gastric acid secretion. As used herein, EGF includes the EGF produced by any of the aforementioned methods and any bioactive fragments, analogs or derivatives and related polypeptides thereof.

The term "analog" of EGF refers to any polypeptide having a substantially identical amino acid sequence to EGF in which one or more amino acids have been substituted with chemically similar amino acids. The term "analog" shall also include any polypeptide which has one or more amino acids deleted from or added to the EGF polypeptide, but which still retains a substantial amino acid sequence homology to EGF. A substantial sequence homology is any homology greater than 50 percent. The term "fragment" of EGF refers to any shorter version of EGF having at least 10 amino acid residues and having the same bioactivity as EGF. The phrase "chemical derivative" refers to any polypeptide derived from the naturally occurring EGF polypeptide in which one or more amino acids have been chemically derivatized synthetically by reaction of functional side groups of the amino acids (i.e. it is derived from the parent EGF molecule by one or more steps).

A "pharmaceutically effective amount" of EGF refers to that amount which provides a therapeutic effect in various administration regimens. For example, when used for wound healing purposes it is that amount which is necessary to enhance the rate of healing a wound. The compositions of the present invention may be prepared containing amounts of EGF within the range of from about 0.01 to about 1,000 micrograms per ml of an aqueous formulation. Preferably, the concentration is in the range 1-500 micrograms per ml and more preferably in the range 1-100 micrograms per ml.

As previously mentioned, EGF degrades over time to form multiple species of the EGF molecule which are believed to be degradation products. Degradation of EGF refers to the natural aging process whereby the molecular structure of the EGF molecule that is used as a starting material (e.g., the 53 amino acid form or a variant thereof) is either: (a) chemically modified to form an EGF variant as a result of a naturally occurring or environmentally induced chemical reaction such as isomerization, oxidation or deamidation; or (b) broken down or decomposed into smaller molecules. Such degradation occurs naturally as a result of environmental factors such as light, which can cause photooxidation; changes in pH; changes in ionic strength; changes in temperature; and physical manipulation of the molecule. Three such degradation products have been identified at this point in time. FIG. 1 depicts a reverse phase HPLC chromatogram of EGF showing the native EGF, designated Peak D, along with the three degradation products, designated Peaks C, X and Y. Stabilized EGF runs as a predominantly single peak (Peak D) on reverse phase HPLC. The major aging products of EGF appear to be those represented by Peaks X and Y. The present invention has been shown to reduce the formation of Peaks X and Y, thus contributing to the maintenance of a predominantly active single species of EGF, i.e., greater than 90% of the starting material remains unchanged.

It is contemplated that the present methods may also be used to stabilize other proteins through the blocking of active amino acid residues with zinc binding. Such other proteins include those in which amino acid residues within the protein structure act to stabilize a degradation product, such as an isomerized intermediate. Also, such other proteins include those which have similar acting amino acid domains to EGF, such as other growth factors, for example fibroblast growth factor.

In the past, certain concentrations of zinc have been reported to exert a stabilizing effect on neutral insulin solutions. See U.S. Pat. No. 4,476,118; and Lougheed, W.D. et al., Diabetologia 19:1-9 (1980). However, zinc was not used to prevent the degradation (as that term is used herein) of the insulin molecule, but rather to prevent precipitation of aggregated insulin from solution. Insulin has a tendency to heterogeneously aggregate and form larger molecular weight aggregates, such as the insulin hexamer, which are not very soluble and tend to precipitate out of solution. The zinc "stabilized" the less soluble hexamer form of insulin by making it more soluble. The early references which reported such a stabilizing effect of zinc used the term "stabilizing" to refer to increased solubility and not degradation, as insulin was not reported to show any significant decrease in biological activity with time. Zinc has also been used as a crystallization promoting metal for insulin and the formation of zinc-insulin crystals. See, U.S. Pat. No. 4,764,592.

As used herein, the terms "zinc", "zinc cation", or "zinc ion" all refer to the divalent zinc ion. Although the present invention is exemplified by the use of the zinc divalent cation, it is contemplated that other suitable cations may achieve the same effect. Such suitable cations must be "pharmaceutically acceptable," which means that they are non-toxic to humans and have no harmful or undesirable side effects when administered to humans, such as inflammation or immunological reaction. Such suitable cations must not cause the degradation of EGF, but rather must be capable of preventing such degradation. Also, such cations must not cause or induce free radical formation. Also, the cations must not adversely effect the biological properties of EGF but rather maintain such properties. Thus, a suitable cation is one that is pharmaceutically acceptable, does not cause free radical formation and has EGF degradation preventing properties and EGF biological activity maintaining properties. It is contemplated that any monovalent, divalent or trivalent cation having such properties is within the scope of the present invention. Lanthanum (trivalent) was shown to form a crystalline precipitate with EGF. Cations of the following metals would not be suitable because they cause free radical formation: manganese, copper, iron and cobalt. Other cations which may be suitable are those of magnesium, calcium, cadmium, nickel, tin, potassium and lithium.

As used herein, "zinc-EGF" or "zinc-EGF complex" refers to a complex ion wherein zinc is coordinately bound to EGF. In aqueous solutions, the zinc-EGF complex must be maintained within the pH range 4.0-7.0, preferably between 5.5 and 6.0. Outside this range the zinc-EGF complex dissociates into monomeric EGF and zinc cation. Thus, it is preferred that aqueous solutions of zinc-EGF are buffered to maintain such a pH range. Any buffer system that maintains the pH within the range 4.0-7.0, preferably 5.5-6.0, is suitable, provided that the counterion present in the buffer does not chelate zinc or otherwise cause it to precipitate from solution. For example, buffer systems which contain phosphate or carbonate are not suitable because they will cause zinc to precipitate. Suitable buffer systems are those based on the following counterions: acetate, succinate, chloride, sulfate, tartrate, malate, maleate and the like. A preferred buffer system is an acetate buffer system. In a preferred embodiment, zinc acetate is added to an EGF solution in order to stabilize the EGF. Zinc acetate has the dual function of providing zinc ions to bind to EGF and acetate counterions to maintain the pH within the preferred range. In the alternative, if another soluble zinc salt such as zinc chloride is used, then a buffer must also be used.

It has been determined that maximum stability of EGF is obtained when about 10-20 mM of zinc cation is added to an aqueous solution of EGF that is at a concentration of about 250 micrograms per ml. Thus, in preferred compositions of the present invention 10-20 mM zinc is used for each 250 micrograms EGF/ml. These amounts may be varied by the skilled practitioner depending on the amount of EGF to be stabilized or the amount of crystalline Zn-EGF that is desired. For example, increasing the EGF concentration would require increasing the amount of zinc proportionately. Higher amounts of zinc, such as up to 50 mM for each 250 micrograms EGF/ml, may also be used to ensure a complete reaction. Lower amounts of zinc such as 5-10 mM, may also be used but all of the EGF may not be stabilized. It is within the capabilities of one skilled in the art to make such variations.

The present invention also provides a crystalline EGF composition which comprises a salt of a complex of zinc and EGF, which has the advantage of long term storability. The cation of the zinc-EGF salt may be any cation that is conducive to salt formation of zinc-EGF, such as: sodium, potassium, lithium, calcium, ammonium, magnesium or barium. As previously mentioned, the zinc-EGF complex will precipitate out of solution provided the pH is within the range 4.0-7.0. Outside this range the complex dissociates. EGF must be dissociated in order for it to have a biological effect in vivo. Thus, zinc-EGF, in aqueous or crystalline form, may be applied directly to a wound or other biological surface in order to provide a slow release formulation for EGF. The physiological pH of the body fluids, i.e. about neutral pH, will cause the zinc-EGF to slowly dissociate to release monomeric EGF.

Crystalline zinc-EGF may be prepared in any number of ways. In general, a soluble zinc salt, such as zinc acetate or zinc chloride, is added to an aqueous mixture of EGF. If necessary, the pH is adjusted to be within the range 4.0–7.0, preferably 5.5–6.0. Crystalline zinc-EGF then precipitates out of solution at room temperature and without mixing. Alternatively, EGF in any form, such as lyophilized form, may be added to a buffered zinc ion solution.

The zinc-EGF crystals may be recovered in any manner known in the art. For example, the aqueous solution containing the crystals may be centrifuged in order to Pack the crystals. Then, the supernatant is poured off and the crystals filtered, washed and then dried.

As EGF has been described as being useful in wound healing, the compositions of the present invention may be used to treat wounds so as to increase the rate of healing thereof. The types of wounds that may be healed using the compositions of the present invention are those which result from any accidental or medical injury which causes epithelial damage, such as ophthalmic wounds, such as those which result from corneal ulcers, radialkeratotomy, corneal transplants, epikeratophakia and other surgically induced wounds in the eye; and cutaneous wounds such as burn wounds, donor site wounds from skin transplants and ulcers (cutaneous, decubitis, venous stasis and diabetic). Additionally, dermatological conditions in which the skin has been damaged, such as psoriasis, sunburn and skin rashes, may be treated with the compositions of the present invention. The compositions may be applied to the wound site either topically or internally depending on the type of wound.

Methods for increasing the rate of healing a wound comprise applying or contacting the compositions of the present invention directly to the wound by topically administering the composition to a wound site. The composition is permitted to remain in contact with the wound for a period of time sufficient to increase the rate of cell growth at the wound site. Such methods include incorporating any composition of the present invention into any pharmaceutically acceptable controlled release composition such as a cream, gel, aerosol spray microcapsules, films or lyophilized foams or aqueous formulation or soaking a gauze dressing with an aqueous solution of the composition and then applying such formulations or dressings to the wound site.

The compositions of the present invention are useful in eyedrop formulations, eye gels, eye creams, liposome or micell formulations, aqueous vehicles for soaking soaked gauze dressings, burn dressings, artificial skins, sutures and staple coatings, salves or creams, gel formulations, foams and the like. Additional materials, such as buffers, preservatives, tonicity adjusting agents, antioxidants, polymers for adjusting viscosity or for use as extenders, and excipients may be used in the compositions. Specific illustrative examples of such other materials include acetate or borate buffers; thimerosol, sorbic acid, methyl or propyl paraben and chlorobutanol preservatives; sodium chloride and/or sugars to adjust the tonicity; and excipients such a mannitol, lactose or sucrose.

The structural stability of EGF as a result of metal binding is a function of the stoichiometry of metal to EGF, pH and ionic strength of the medium. Another important variable in the metal-protein complex formation is the dielectric constant (DIE) and the water activity on the surface of the protein. Neutral compounds have been shown to affect the water structure and the DIE in the medium. A decrease in the DIE should cause an increase in ionic interaction (e.g., metal-EGF complex), thereby enhancing the binding of the metal to EGF and increasing the stability. A secondary effect of decreasing the DIE would be to increase intramolecular hydrogen bonding, which would also contribute to the EGF stability. Thus, it is believed that factors which decrease the DIE will have a stabilizing effect on the EGF protein by changing the polarity of the water, altering the hydration envelope around the protein and in some cases interacting directly with the surface of the protein. Examples of neutral compounds which are capable of reducing the DIE are as follows: monohydric and polyhydric alcohols, such as ethanol, isopropanol, mannitol, sorbitol, inositol, sucrose, lactose, glycerin, and the like; polyhydroxylic compounds, such as glycerol, polyethylene glycol, propylene glycol, polyoxmer (Pluronic F-68), povidone, hydroxymethyl (ethyl or propyl) cellulose, octoxynol-9, and the like; surfactants, such as polysorbate (Tweens), Brij, polyoxyethylene sorbitan monoester and triester, and the like; amino acids, such as glycine, leucine, polyamino acids, and the like; and other compounds such as gelatin or hydrolyzed gelatin and dextran. Such compounds are all FDA approved and water soluble. It is believed that addition of any of these neutral charged pharmaceutical compounds to the compositions of the present invention may further increase the stabilization of the EGF.

The present compositions may also be combined with anti-bacterial compounds, such as sulfadiazine compounds and in particular silver sulfadiazine and zinc sulfadiazine. A zinc sulfadiazine compound would have the dual purpose of providing antibacterial and stabilizing properties to the composition.

The compositions of the present invention may be lyophilized in order to provide further stability of the EGF. Methods of lyophilization are well known in the art. Stable lyophilized formulations containing growth factors are described in copending and commonly assigned U.S. Ser. No. 098,817, the contents of which is hereby incorporated by reference into this disclosure.

The following examples are presented to illustrate the subject invention. The invention is not to be considered limited by these examples but only by the appended claims.

EXAMPLE 1

Recombinantly produced human EGF (Chiron Corporation, Emeryville, Calif.) was used in the following experiments. EGF stability with zinc ion was tested at pH 5.5 to 6.5. Lyophilized EGF was reconstituted in 50 mM sodium acetate at PH 5.5. A solution of zinc chloride was then added to this EGF solution. Alternatively, a solution of zinc acetate or crystals of a zinc salt could have been added. The pH was maintained in the range 5.5 to 6.5 and zinc-EGF precipitated out of solution at room temperature.

The samples were permitted to age over a 28 day period and then HPLC analysis was used to study the structural changes involving the formation of new species (e.g., Peaks C, X and Y) of EGF under various storage conditions and in the presence of new formulations. Reverse phase HPLC can be used for quantitative and qualitative analysis of EGF. The HPLC results are set forth below in Table 1.

The zinc-EGF complex must be dissociated before HPLC analysis because the complex cannot be run on the HPLC column as is. Therefore, prior to HPLC, the pH of the samples to be analyzed was adjusted to 3.0. Alternatively, EDTA (a chelating agent) may be used to reverse crystallization. Reverse phase HPLC was conducted using a Vydac C-4 column (4.6 mm×25 cm, 5μm). The flow rate was 0.8 ml/min at 26° C. using a linear gradient of 26% to 32% acetonitrile (0.1% TFA) over 26 minutes.

TABLE 1

| | EGF at various pH's for 28 Days at 46° C. | | | | | |
|---|---|---|---|---|---|---|
| | With Zn++ | | | Without Zn++ | | |
| pH | 5.5 | 6.0 | 6.5 | 5.5 | 6.0 | 6.5 |
| % Peaks | | | | | | |
| C | 3 | 3 | 1 | 3 | 6 | 6 |
| D | 82 | 75 | 86 | 30 | 51 | 52 |
| Y | 14 | 15 | 13 | 25 | 21 | 21 |
| X | 0 | 4 | 0 | 42 | 20 | 21 |

As can be seen from Table 1, the formation of the degradation species represented by Peaks Y and X was greatly reduced when EGF was formulated in the presence of zinc ion when compared to formulations that did not have zinc ion. Further testing showed that the Peak X and Y species had a 40% loss in biological activity over the Peak D native EGF. The Peak C species showed no change in biological activity. Thus, stabilization of EGF with zinc results in a significant increase in EGF biological activity by reducing the formation of the Peak X and Y species.

EXAMPLE 2

This experiment was designed to answer the stability of the zinc-EGF complex results from the exclusion of water by the large and insoluble complex or alternatively from the direct interaction of zinc ion with specific amino acids in the protein. A zinc-EGF solution and control were prepared as in Example 1 and the samples were adjusted to a PH of 4.6. At this pH EGF naturally precipitates out of solution since it is at its isoelectric point. Two sets of the precipitated EGF at pH 4.6 in sodium acetate buffer were incubated for 7 days at 46° C. One set had zinc ion present, the other did not. The HPLC results are set forth in Table 2 below.

TABLE 2

| | EGF at pH 4.6 for 7 Days at 46° C. | |
|---|---|---|
| % Peaks | With Zn++ | Without Zn++ |
| C | 2 | 0 |
| D | 91 | 47 |
| Y | 0 | 27 |
| X | 7 | 26 |

Table 2 shows that the zinc-EGF complex has a significant decrease in Peaks X and Y compared to the formulation containing EGF alone in precipitated form. This suggests that a direct interaction of zinc with EGF is important and that the zinc-EGF complex is stable in both aqueous and crystalline forms.

EXAMPLE 3

For the purposes of this application, the biological activity of the zinc-EGF complex was tested in the receptor binding assay (RBA). This assay measures the binding of EGF to its receptor and the assay has a variability range of 15-30%. It is an accepted method of determining the biological activity of EGF. The receptor binding assay method used was that of Savage et al., Analytical Biochem, 111. pages 195 et seq. (1981). The RBA is also described and set forth in U.S. Pat. No. 4,717,717, the disclosure of which is incorporated by reference into this specification. EGF at a concentration of 100 micrograms per ml was mixed with zinc ion resulting in precipitation. The precipitated material was split into two equal volumes. EDTA was added to one sample at twice the molar level of the zinc ion. This resulted in a clear solution with no precipitation. The other sample was left unchanged in a precipitated form and the three samples were assayed on the RBA and the results are set forth in Table 3. The buffer used in the RBA was a phosphate buffer at pH 7.4. At this pH, the Zn-EGF dissociated into its monomeric form and the zinc precipitated as zinc phosphate. EGF without zinc was treated as a control.

TABLE 3

| | (micrograms per ml) | |
|---|---|---|
| Zn-EDTA, EGF | precipitated Zn-EGF | EGF only |
| 135 ± 5 | 140 ± 20 | 138 ± 10 |

The results in Table 3 show that there was no loss of EGF activity in the presence of zinc in precipitated form, which suggests that the zinc-EGF complex is reversible.

The invention has been described herein with reference to certain preferred embodiments and examples. Since obvious variations will appear to those skilled in the art, the invention is not to be considered limited thereto but only by the claims which follow.

What is claimed is:

1. A crystalline EGF composition which comprises a salt of a complex of zinc and EGF.

2. A method for the preparation of the composition of claim 1, comprising the steps of formulating said EGF and zinc ions.

3. The composition of claim 1 which is a buffered aqueous solution.

4. The composition of claim 1, which is a gel.

5. The composition of claim 1, which is a cream.

6. The composition of claim 1, which further comprises a neutral dielectric constant reducing compound.

7. The composition of claim 1 which has a PH within the range of about 4.0 to about 7.0.

8. The composition of claim 7 wherein the pH is within the range of about 5.5 to about 6.0.

9. The composition of claim 1 which has about 10-20 mM of zinc cation per 250 micrograms EGF/ml.

10. The composition of claim 3 wherein the buffer is an acetate buffer.

11. A method for producing crystalline human EGF, comprising:
   a) providing an aqueous solution of EGF;
   b) adding zinc, in aqueous or solid form, to said EGF solution, to form a mixture of zinc and EGF wherein 10-20 mM of zinc is used per 250 micrograms EGF/ml;
   c) adjusting the pH of said mixture to a pH within the range of 4.0 to 7.0;
   d) allowing zinc-EGF crystal formation to occur; and
   e) recovering crystalline zinc-EGF from the mixture.

* * * * *